United States Patent [19]
Wong

[11] Patent Number: 5,162,513
[45] Date of Patent: Nov. 10, 1992

[54] L-ISOMERIC SUGARS HAVING FORMED STEREOGENIC CENTERS OF R CONFIGURATION: METHODS AND COMPOSITIONS

[75] Inventor: Chi-Huey Wong, San Diego, Calif.

[73] Assignee: The Scripps Research Institute, La Jolla, Calif.

[21] Appl. No.: 763,359

[22] Filed: Sep. 20, 1991

[51] Int. Cl.$^5$ .......... C12N 9/88; C12P 19/02; C07H 1/00; C07H 1/06
[52] U.S. Cl. .......... 536/1.1; 536/6; 536/18.6; 435/232; 435/105
[58] Field of Search .......... 536/1.1, 22, 6, 18.6; 435/190, 232, 105

[56] References Cited

U.S. PATENT DOCUMENTS

| | | | |
|---|---|---|---|
| 4,207,413 | 6/1980 | Szarek et al. | 536/1.1 |
| 4,367,226 | 1/1983 | Foye | 536/22 |
| 4,371,616 | 2/1983 | Huibers | 536/1.1 |
| 4,699,883 | 10/1987 | Sugimori et al. | 435/232 |

OTHER PUBLICATIONS

Auge et al., Tetrahedron vol. 46, No. 1, pp. 201–214 (1990).
Shukla et al., Analytical Biochemistry 158, 158–164 (1986).
Auge et al., New J. Chem. 12, p. 733 (1988).
Deijl et al., Biochem. & Biophy. Res. Comm. vol 111, No. 2, (1983).
The Merck Index, tenth ed., Merck & Co., Inc. (1983).
Bergey's Manual of Determinative Bacteriology, eighth ed., The Williams & Wilkins Co. (1974).
Auge et al; Tetrahedron Letters, 30(17), pp. 2217–2220; 1989; "Scope & limitations of the aldol condensation catalyzed by immobilized acylneuraminate pyruvate lyase".
Auge et al; Journal Chemical Society, Chemical Communication, (11) pp. 859–860; 1987; "Use of an immobilized aldolase in the first synthesis of a natural deaminated neuraminic acid".

*Primary Examiner*—Ronald W. Griffin
*Assistant Examiner*—Louise Leary
*Attorney, Agent, or Firm*—Dressler, Goldsmith, Shore, Sutker & Milnamow, Ltd.

[57] ABSTRACT

The present invention provides L-isomeric nine-carbon sugars having a formed stereogenic center of R configuration, as well as methods of synthesizing the same.

6 Claims, No Drawings

L-ISOMERIC SUGARS HAVING FORMED STEREOGENIC CENTERS OF R CONFIGURATION: METHODS AND COMPOSITIONS

This invention was made with the support of the U.S. Government, and the U.S. Government has certain rights in the invention.

TECHNICAL FIELD OF THE INVENTION

The present invention relates to L-isomeric sugars having formed stereogenic centers of R configuration and methods for synthesizing such sugars using sialic acid aldolase.

BACKGROUND OF THE INVENTION

A major synthetic value of enzyme catalysis is its usually predictable stereoselectivity. See, e.g., Whitesides et al., *Angew. Chem. Int. Ed. Encl.*, 24:617 (1985); Jones, J. B. *Tetrahedron*, 42:3351 (1986); Yamada et al., *Angew. Chem. Int. Ed. Engl.*, 27:622 (1988); Wong, C.-H., *Science*, 244:1145 (1989); Ohno et al., *Org. React.* 37:1 (1989); Chen et al., *Angew. Chem. Int. Ed. Engl.*, 28:695 (1989).

A change of stereoselectivity, however, may occur, though very unusual, with different substrate structures, temperatures or solvents. See, e.g., Mohr et al., *Helv. Chim. Acta*, 66:2501 (1983); Sabbioni et al., *J. Chem. Soc. Chem. Commun.*, 236 (1984); Ohno et al., *J. Am. Chem. Soc.* 103:2405 (1983); Wang et al., *J. Org. Chem.* 53:3127 (1988); Lalonde et al., *J. Am. Chem. Soc.* 103:2405 (1981); Wang et al., *J. Org. Chem.*, 53:2323 (1988); Pham et al., *J. Am. Chem. Soc.*, 111:1935 (1989); Keinan et al., *J. Am. Chem. Soc.*, 108:162 (1986); Sakurai et al., *J. Am. Chem. Soc.*, 110:7236 (1988); Fitzpatrick et al., *J. Am. Chem. Soc.* 113:3166 (1991). These selectivity changes are often not very significant, with some exceptions where the enantioselectivity is inverted.

In the case of enzymatic aldol reactions, the diastereofacial selectivity for the aldehyde component is often consistent and completely controlled by the enzyme as documented by numerous reactions catalyzed by fructose-1,6-diphosphate aldolase or N-acetylneuraminic acid (or sialic acid) aldolase (EC 4.1.3.3). In most cases, the "D" isomer of an α-substituted aldehyde reacts faster than the "L" isomer, both with si-facial selectivity. The Cram-Felkin mode of attack on the "D" aldehyde is therefore proposed for the transition state. See, e.g., Toone et al., *Tetrahedron*, 45:5365 (1989); Bednarski et al., *J. Am. Chem. Soc.*, 111:627 (1989); Straub et al., *J. Org. Chem.*, 55:3926 (1990); Durrwachter et al., *J. Org. Chem.*, 53:4175 (1988); von der Osten et al., *J. Am. Chem. Soc.*, 111:3924 (1989); Kajimoto et al., *J. Am. Chem. Soc.*, 113:6187 (1991); Auge et al., *New J. Chem.*, 12:733 (1988).

Because of the stereoselectivity of enzymes such as aldolases that participate in the metabolism of carbohydrates, it is extremely difficult to design and make new carbohydrates that can be used to study carbohydrate metabolism. There is a need for such synthetic compounds for use as experimental tools in elucidating the molecular character of the numerous and varied pathways involved in carbohydrate anabolism and catabolism.

Of particular relevance to the present invention is the sugar, N-acetylneuraminic acid (NeuAc) or sialic acid. NeuAc is an integral component of most cells and is believed to play a major role in imparting electrical charge characteristics to such cells. Further, NeuAc-like compounds such as the eight and nine-carbon sugar moieties KDO and KDN are major constituents of non-mammalian tissues.

N-Acetylneuraminic Acid (NeuAc) aldolase, also commonly referred to as sialic acid aldolase is a type I aldolase known to form an enamine intermediate with pyruvate, which reversibly reacts with the second substrate N-acetylmannosamine to give NeuAc. See, e.g., Deijl et al., *Biochem. Biophys. Res. Commun.*, 111:668 (1983); and Shukla et al., *Anal. Biochem.*, 158:158 (1986).

NeuAc aldolase is known to accept many aldoses as acceptor substrates. In all previously known aldol condensation reactions with such acceptor substrates, the eneamine intermediate approaches the si face of the incoming aldehyde substrate to form a new stereogenic center of S configuration. Anti-Cram-Felkin attack is generally observed for good chiral aldehyde substrates and Cram-Felkin attack is observed for weak substrates. In both cases, a si-facial selectivity was observed. See, e.g., Auge et al., *New J. Chem.*, 12:733 (1988); and Auge et al., *Tetrahedron*, 46:201 (1990).

Based on such current knowledge concerning aldolase stereoselectivity, therefore, NeuAc aldolase is considered to be useful only for the production of D-sugars having S configuration. As is disclosed hereinafter, NeuAc aldolase has now unexpectedly been found to be capable of the production of certain L-sugars having a formed stereogenic center of R configuration.

BRIEF SUMMARY OF THE INVENTION

In another aspect, the present invention contemplates L-sugars having a formed sterogenic center of R configuration. More particularly, the present invention contemplates compounds having the Formulae I, II, III and IV, below:

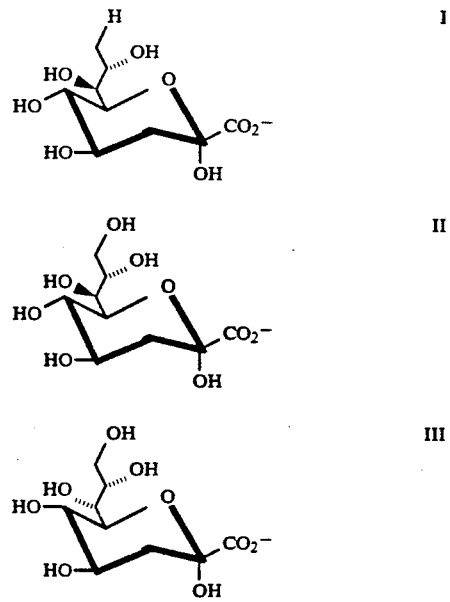

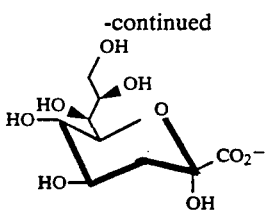

In another aspect, the present invention contemplates a method of synthesizing the compounds of Formula I, II, III or IV comprising the steps of:

a) admixing pyruvate, in the presence of a catalytic amount of NeuAc aldolase, with an acceptor substrate L-rhamnose, L-mannose, L-talose or D-gulose, respectively, to form a reaction mixture; and b) maintaining the reaction mixture for a time period and under biological reaction conditions sufficient for condensation of the pyruvate with the acceptor substrate and formation of a compound of Formula I, II, III or IV, above.

In a preferred embodiment, the synthetic method further comprises recovering the synthesized compound of Formula I, II, III, or IV.

DETAILED DESCRIPTION OF THE INVENTION

A. Compounds

The present invention contemplates L-isomeric nine-carbon sugars. The nine-carbon L-sugar compounds have the Formula I, II, III, or IV, below:

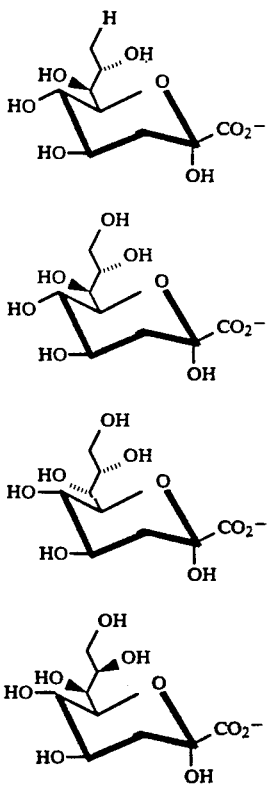

Formula I defines 3,9-dideoxy-L-glycero-L-galactononulosonic acid. Given that 3,9-dideoxy-D-glycero-D-galactononulosonic acid defines D-9-deoxy KDN, the compound of Formula I can also be referred to as L-9-deoxy KDN.

Formula II defines 3-deoxy-L-glycero-L-galactononulosonic acid, which can also be referred to as L-KDN.

The compounds of Formulae I-IV have a $^5C_2$ conformation as evidenced by the adjacent transaxial coupling of protons at the carbon atoms at positions 3, 4 and 5. Further, the compounds of Formulae I-IV have a formed stereogenic center of R configuration.

The compounds of Formula I, II, III and IV synthesized in accordance with the method described herein have a formed stereogenic center of R configuration that is created via the re attack of pyruvate on the acceptor substrate. This re attack and resulting R configuration are surprising and unexpected in view of the published literature. In all previously known aldol condensation reactions using NeuAc aldolase, the attack is on the si face of the acceptor substrate and the resulting condensation product has a formed stereogenic center of S configuration. See, e.g., Auge et al., *New J. Chem.*, 12:733 (1988); Auge et al., *Tetrahedron*, 46:201 (1990); and Kim et al., *J. Am. Chem. Soc.*, 110:6481 (1988).

Thus, where mannosamine (ManNAc), mannose (Man), 4-deoxy-man, 2-deoxy-2-phenyl-Man, 6-O-Ac-ManNAc, 6-O-Ac-2-deoxy-glucose (Glc), 6-deoxy-6-$N_3$-ManNAc, 6-deoxy-6-F-ManNAc, 4,6-dideoxy-4,6-$F_2$-talose, D-Glc, D-altose, 2-deoxy-galactose (Gal), Glucosamine (GlcNAc), D-lyxose, D-arabinose or 2-deoxy-ribose was reacted with pyruvate and a catalytic amount of NeuAc aldolase, the resulting condensation products were all found to have formed stereogenic centers of S configuration resulting from a si facial attack. Wong, C.-H., *Microbial Aldolases* in *Enzymes in Carbohydrate Synthesis* ed. by Bednarski and Simon, American Chemical Society, ACS Symposium Series No. 466 (1991).

The re attack and resulting R configuration where L-rhamnose, L-mannose, L-talose and D-gulose were used as the acceptor substrate are even more surprising and unexpected because such reversal of stereo-selectivity was not observed with all L-isomeric acceptor substrates. Where L-glucose or L-fucose were reacted with pyruvate in the presence of NeuAc aldolase, no aldol condensation product was formed. Wong, C.-H., *Microbial Aldolases* in *Enzymes in Carbohydrate Synthesis* ed. by Bednarski and Simon, American Chemical Society, ACS Symposium Series No. 466 (1991)

B. Synthetic Method

Another aspect of the present invention contemplates an aldol condensation method of synthesizing the compounds of Formulae I-IV. In accordance with the aldol condensation method, pyruvate (typically in excess) is admixed in the presence of a catalytic amount of NeuAc aldolase, with an acceptor substrate to form a reaction mixture. The reaction mixture is maintained for a time period and under biological reaction conditions sufficient to condense the pyruvate and acceptor substrate and form a compound of Formulae I, II, III or IV.

The structure of the acceptor substrate dictates the structure of the synthesized aldol condensation product. Where the acceptor substrate is L-rhamnose, the compound of Formula I is synthesized. Where the acceptor substrate is L-mannose, the compound of Formula II is synthesized. Where the acceptor substrate is L-talose, the compound of Formula III is synthesized. Where the acceptor substrate is D-gulose, the compound of Formula IV is synthesized.

Pyruvate is readily available from commercial sources (Sigma Chemical Co., St. Louis, Mo.). A preferred formulation of pyruvate is sodium pyruvate. L-Mannose, L-rhamnose, L-talose and D-gulose are also available from Sigma Chemical Co.

Highly stable NeuAc aldolase in a free or immobilized form is readily available. See, e.g., Auge et al., *New J. Chem.*, 12:733 (1988); Auge et al., *Tetrahedron*. 46:201 (1990); and Kim et al., *J. Am. Chem. Soc.*, 110:6481 (1988).

As used herein, the phrase "catalytic amount" means that amount of NeuAc aldolase at least sufficient to catalyze, in a non-rate limiting manner, the condensation of pyruvate and acceptor substrate to product.

The catalytic amount of NeuAc aldolase varies according to the specific activity of NeuAc aldolase (Units/mg), the concentration of acceptor substrate as well as biological reaction conditions such as temperature, time and pH value. Means for determining the catalytic amount of NeuAc aldolase under preselected substrate concentrations and biological reaction conditions are well known to those of skill in the art. Typical amounts range from about 5 to about 20 Units (U) per millimole (mmol) of acceptor substrate, with about 10 to about 15 U/mmol typically being used.

Each ingredient is admixed with each of the other ingredients in a suitable aqueous solvent to from a reaction mixture. The reaction mixture is maintained under biological reaction conditions (temperature, pH, solvent osmolality, ionic composition and ambient pressure) for a period of time sufficient to condense the substrate acceptor and pyruvate to form a compound of Formula I, II, III or IV.

Temperature can range from about 15° C. to about 40° C. Preferably, temperature is from about 20° C. to about 40° C. and, more preferably from about 25° C. to about 37° C.

The pH value can range from about 6.0 to about 11.0. Preferably, the pH value is from about 6.0 to about 8.5 and, more preferably from about 7.0 to about 7.5. The pH value is maintained by buffers in the aqueous solvent. A preferred buffer is potassium phosphate.

The aqueous solvent preferably further comprises an anti-oxidant. A preferred anti-oxidant is a sulfur-containing reducing agent such as a mercaptan (thiol). Exemplary mercaptans are mercaptoethanol and dithiothreitol.

The reaction time varies with the temperature and the activity of the NeuAc aldolase. Where the NeuAc aldolase has an activity of about 10 Units, the temperature is about 37° C., and the concentration of acceptor substrate is about 1 mM, the reaction time is about 48 hours (See Examples 1 and 2 hereafter).

The synthetic method of the present invention can further include recovering a synthesized compound of Formula I, II, III or IV. Recovering comprises isolating the synthesized compound from the reaction mixture. Means for isolating a synthesized compound of Formula I, II, III or IV include gel filtration, column chromatography, paper chromatography, affinity chromatography, extraction, precipitation and the like.

In a preferred embodiment, isolation is accomplished by applying a reaction mixture containing about 1 mM acceptor substrate to an anion exchange chromatography column of Dowex 1×8-100 (HCOO− form; 30×2 cm) and eluting a compound of Formula I, II, III or IV with formic acid (0.2M). Where such an embodiment is used for isolation, a compound of Formula I can typically be recovered with a yield of about 80% (See Example 1).

The reaction rate of the method of the present invention is substantially the same as the reaction rate of NeuAc aldolase-catalyzed condensation of pyruvate with acceptor substrates having an enantiomeric configuration (i.e., D-rhamnose, D-mannose, D-talose, L-gulose). The substantial similarity of the reaction rates with D- and L-configured acceptor substrates is surprising and unexpected. With aldolases other than NeuAc aldolase (i.e., fructose-1,6-diphosphate aldolase), the reaction rate is markedly faster with D-configured acceptor substrates than with L-configured acceptor substrates. See, e.g., Toone et al., *Tetrahedron*, 45:5365 (1989); Bednarski et al., *J. Am. Chem. Soc.*, 111:627 (1989); Straub et al., *J. Org. Chem.*, 55:3926 (1990); Durrwachter et al., *J. Org. Chem.*, 53:4175 (1988); von der Osten et al., *J. Am. Chem. Soc.*, 111:3924 (1989); Kajimoto et al., *J. Am. Chem. Soc.*, 113:6187 (1991);

The following Examples illustrate particular embodiments of the present invention and are not limiting of the specification and claims in any way.

EXAMPLE 1

Synthesis of 3,9-Dideoxy-L-glycero-L-galactononulosonic acid (L-9-deoxy KDN) Compound of Formula I A 0.1M solution of L-rhamnose (1 mmol) in a 0.05M potassium phosphate buffer, pH 7.2, containing 0.01M dithiothreitol, sodium pyruvate (3 equivalent) and 10 U of NeuAc aldolase was incubated at 37° C. (total volume = 10 mL) for 2 days. The reaction was monitored by TLC (PrOH/water=7:3 v/v).

The title product was isolated by anion exchange chromatography on Dowex 1×8-100 (HCOO− form; 30×2 cm) using a gradient of formic acid (0.2M) as eluant. Fractions containing the product were pooled and freeze-dried. Yield 200 mg (80%).

$^1$H-NMR (500 MHz, D$_2$O) d 1.08 (d, J$_{8,CH3}$=6.5 Hz, CH$_3$), 1.62 (dd, J$_{3ax,3eq}$=13.3 Hz, J$_{3ax,4}$=11.5 Hz, H$_{3ax}$), 2.06 (dd, J$_{3eq,4}$=6.7 Hz, H$_{3eq}$), 3.39 (t, J$_{4,5}$=J$_{5,6}$=9.5 Hz, H-5), 3.675 (dd, J$_{6,7}$=0.8 Hz, J$_{7,8}$=8.2 Hz, H-7), 3.66 (dd, H-8), 3.8 (dd, H-6), 3.76–3.83 (ddd, H-4). $^{13}$C-NMR (125 MHz, reference CH$_3$CN 1.6), 175.3800 (C-1), 96.1195 (C-2), 72.7438 (C-8), 72.3426 (C-6), 70.9565 (C-5), 69.3967 (C-7), 67.4548 (C-4), 39.325 (C-3), 19.8777 (CH$_3$); [a]$_D^{20}$ +60 (c 1.2, water); HRMS for C$_9$H$_{15}$O$_8$ calcd. 253.0923, found 253.0923.

Example 2:

Synthesis of 3-Deoxy-L-glycero-L-galactononulosonic acid (L-KDN) Compound of Formula II A 0.1M solution of L-mannose (1 mmol) in a 0.05M potassium phosphate buffer, pH 7.2, containing 0.01M dithiothreitol, sodium pyruvate (3 equivalent) and 10 U of NeuAc aldolase was incubated at 37° C. (total volume = 10 mL) for 2 days. The reaction was monitored by TLC (PrOH/water=7:3 v/v).

The title product was isolated by anion exchange chromatography on Dowex 1×8-100 (HCOO− form; 30×2 cm) using a gradient of formic acid (0.2M) as eluant. Fractions containing the product were pooled and freezedried. Yield 200 mg (80%).

The physical data ($^1$H, $^{13}$C-NMR and HRMS) were identical to the reported values of D-KDN except for the specific rotation $[[\alpha]_D^{20} -60° (c\ 1.2, H_2O)]$.

EXAMPLE 3

Synthesis of Compounds of Formulae III and IV

The compounds of Formulae III and IV were synthesized in accordance with the procedures of Examples 2 and 3. The compounds of Formulae III and IV were L-isomeric sugars and had formed stereogenic centers of R configuration.

The foregoing is intended as illustrative of the present invention but not limiting. Numerous variations and modifications may be effected without departing from the true spirit and scope of the novel concepts of the invention.

We claim:

1. A compound of the Formula I:

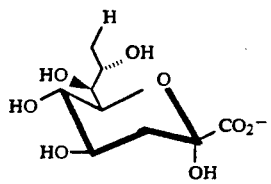

2. A compound of the Formula II:

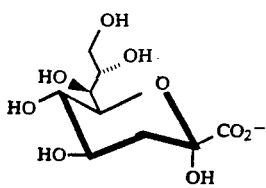

3. A compound of the Formula III:

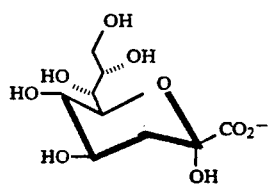

4. A compound of the Formula IV:

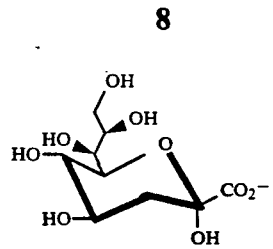

5. A method of synthesizing a compound of the Formula I, II, III or IV, below:

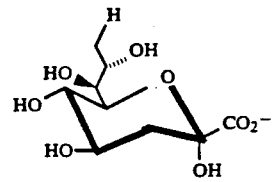

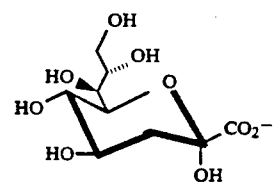

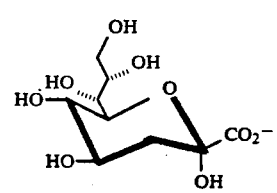

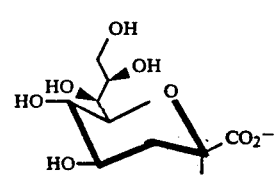

comprising the steps of:
a) admixing in an aqueous solvent pyruvate, in the presence of a catalytic amount of sialic acid aldolase (E.C.4.1.3.3.), with an acceptor substrate L-rhamnose, L-mannose, L-talose or D-gulose, respectively, to form a reaction mixture; and
b) maintaining the reaction mixture for a time period and under biological reaction conditions sufficient for condensation of said pyruvate with said acceptor substrate and formation of a compound of Formula I, II, III or IV.

6. The method according to claim 5 further comprising recovering the synthesized compound of Formula I, II, III or IV.

* * * * *